(12) United States Patent
Stokes et al.

(10) Patent No.: US 11,937,820 B2
(45) Date of Patent: *Mar. 26, 2024

(54) JAW FOR CLIP APPLIER

(71) Applicant: Cilag GmbH International, Zug (CH)

(72) Inventors: Michael J. Stokes, Cincinnati, OH (US); Chester O. Baxter, III, Loveland, OH (US); Carol J. Wynn, Kings Mills, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 123 days.

This patent is subject to a terminal disclaimer.

(21) Appl. No.: 17/181,251

(22) Filed: Feb. 22, 2021

(65) Prior Publication Data

US 2021/0169483 A1 Jun. 10, 2021

Related U.S. Application Data

(63) Continuation of application No. 15/674,121, filed on Aug. 10, 2017, now Pat. No. 10,959,732.

(51) Int. Cl.
*A61B 17/10* (2006.01)
*A61B 17/128* (2006.01)
(Continued)

(52) U.S. Cl.
CPC ............ *A61B 17/105* (2013.01); *A61B 17/10* (2013.01); *A61B 17/128* (2013.01);
(Continued)

(58) Field of Classification Search
CPC . A61B 17/068; A61B 17/0682; A61B 17/128; A61B 17/1285; A61B 17/105; A61B 2017/00862
See application file for complete search history.

(56) References Cited

U.S. PATENT DOCUMENTS 4,509,518 A 4/1985 McGarry et al.
4,979,950 A 12/1990 Transue et al.
(Continued)

FOREIGN PATENT DOCUMENTS

CN 102647948 A 8/2012
CN 102860850 A 1/2013
(Continued)

OTHER PUBLICATIONS

European Search Report received for European Patent Application No. 18188269.7, dated Nov. 15, 2018, 8 pages.
(Continued)

*Primary Examiner* — Diane D Yabut
(74) *Attorney, Agent, or Firm* — Mintz Levin Cohn Ferris Glovsky and Popeo, P.C.

(57) ABSTRACT

Jaws of a surgical clip applier with housings formed thereon and methods for manufacturing and use during a procedure to apply surgical clips to a vessel, duct, shunt, etc. are provided. In one exemplary embodiment, a surgical clip applier is provided having jaws on a distal end thereof with a rigid internal frame and an outer housing formed around the internal frame. The jaws of the surgical clip applier can include a variety of features to facilitate placement of surgical clips, including features to align a clip with the jaws and to prevent clip fallout during formation.

20 Claims, 13 Drawing Sheets

(51) Int. Cl.
  *A61B 17/00* (2006.01)
  *A61B 17/28* (2006.01)
  *A61B 17/29* (2006.01)
  *B29C 45/14* (2006.01)
  *B29L 31/00* (2006.01)

(52) U.S. Cl.
  CPC ............... *A61B 17/1285* (2013.01); *A61B 2017/00367* (2013.01); *A61B 2017/00526* (2013.01); *A61B 2017/00862* (2013.01); *A61B 2017/00964* (2013.01); *A61B 2017/2825* (2013.01); *A61B 2017/2915* (2013.01); *A61B 2017/2916* (2013.01); *A61B 2017/2933* (2013.01); *A61B 2017/2936* (2013.01); *A61B 2017/2937* (2013.01); *A61B 2017/2945* (2013.01); *B29C 45/14* (2013.01); *B29L 2031/7546* (2013.01)

(56) References Cited

U.S. PATENT DOCUMENTS

| | | | |
|---|---|---|---|
| 5,100,420 A * | 3/1992 | Green | A61B 17/1285 227/19 |
| 5,431,668 A | 7/1995 | Burbank et al. | |
| 5,681,330 A | 10/1997 | Hughett et al. | |
| 6,824,547 B2 | 11/2004 | Wilson, Jr. et al. | |
| 10,675,031 B2 | 6/2020 | Stokes et al. | |
| 2004/0097971 A1 | 5/2004 | Hughett | |
| 2005/0171560 A1 | 8/2005 | Hughett | |
| 2008/0188872 A1 | 8/2008 | Duff | |
| 2010/0274262 A1 | 10/2010 | Schulz et al. | |
| 2012/0109158 A1 | 5/2012 | Zammataro | |
| 2015/0080879 A1 | 3/2015 | Trees et al. | |
| 2019/0046197 A1 | 2/2019 | Stokes et al. | |
| 2019/0046198 A1 | 2/2019 | Stokes et al. | |
| 2020/0297347 A1 | 9/2020 | Stokes et al. | |

FOREIGN PATENT DOCUMENTS

| | | |
|---|---|---|
| CN | 203388963 U | 1/2014 |
| CN | 103732174 A | 4/2014 |
| CN | 106456185 A | 2/2017 |
| CN | 106491177 A | 3/2017 |
| EP | 0598529 A2 | 5/1994 |
| JP | H05337124 A | 12/1993 |
| JP | 2004344488 A | 12/2004 |
| JP | 2012096008 A | 5/2012 |
| WO | 03099137 A2 | 12/2003 |
| WO | 2016192096 A1 | 12/2016 |

OTHER PUBLICATIONS

International Preliminary Report on Patentability for Application No. PCT/IB2018/055953, dated Feb. 20, 2020, 9 pages.
International Preliminary Report on Patentability received for PCT Application No. PCT/IB2018/055948, dated Feb. 20, 2020, 11 pages.
International Search Report and Written Opinion received for PCT Application No. PCT/IB2018/055953, dated Nov. 15, 2018, 16 pages.
International Search Report and Written Opinionreceived for PCT Application No. PCT/IB2018/055948, dated Nov. 26, 2018, 18 pages.

* cited by examiner

JAW FOR CLIP APPLIER

CROSS REFERENCE TO RELATED APPLICATIONS

This application is a continuation of U.S. patent application Ser. No. 15/674,121, filed Aug. 10, 2017, entitled "Jaw for Clip Applier," which is hereby incorporated herein by reference in its entirety.

FIELD

Clip appliers having an improved jaw structure, and methods for using and manufacturing the same, are provided herein.

BACKGROUND

A variety of surgical procedures require application of clips to seal and/or secure tissue, requiring a surgical clip applier for ligating a blood vessel, a duct, shunt, a portion of body tissue, etc. during surgery. The jaws of most surgical clip appliers are formed through a process of metal stamping or machining, which can limit the possible geometry of the jaws. For example, rails of the jaws are designed to hold a clip in a clip track, however sufficient clearance is required in order to accommodate varying clip heights or other deformities between clips. This clearance can result in surgical clips being free to shift or wiggle in the clip tracks, which could result in clip malformation or clip fallout.

Accordingly, there remains a need for clip appliers having an improved structure for formation and placement of clips during surgical procedures.

SUMMARY

Clip appliers having improved jaws and methods for using and manufacturing the same are provided herein. In one embodiment, a surgical clip applier is provided and includes an elongate shaft and a jaw assembly at a distal end of the elongate shaft. The jaw assembly can include a metal frame having a proximal portion coupled to the elongate shaft and a distal portion including first and second jaws movable between open and closed positions for engaging tissue therebetween. The first and second jaws can each have an engagement feature formed thereon. The jaw assembly can also include a first outer housing around the first jaw and a second outer housing around the second jaw. The engagement feature can prevent movement of the first and second outer housings relative to the metal frame. The first and second outer housings can also have opposed inward facing surfaces, with each inward facing surface having a clip track formed therein and extending longitudinally therealong for receiving and guiding a clip into the jaws.

In one embodiment, the first and second outer housings can be overmolded around the first and second jaws, and in another embodiment, the first and second outer housings can be configured to be coupled to the first and second jaws through one of adhesive, welding, and mechanical engagement means.

In some embodiments, the first and second jaws can include opposed inward facing surfaces, and the engagement feature can be a protrusion formed on the inward facing surface. The protrusion on each of the first and second jaws can extend through the outer housing such that the protrusion is configured to contact a clip seated in the clip track.

The jaw assembly can be formed from various materials. In one embodiment, the first and second outer housings can be formed from a polymeric material. The metal frame can have a modulus of elasticity that is greater than a modulus of elasticity of a material forming the first and second outer housings.

The housings can include various features. For example, the first and second outer housings can each include a plurality of fingers protruding into the clip track for retaining a clip therein. The plurality of fingers can be flexible. The first and second outer housings can also each include upper and lower rails that define the clip track. In one embodiment, at least one cut-out can be formed in at least one of the upper and lower rails for allowing a user to view a clip seated in the clip track. In other embodiments, the first and second outer housings can each have upper and lower protrusions positioned on opposed sides of the clip track for retaining a clip seated in the clip track.

In another embodiment, a jaw insert for use with a clip applier device is provided and includes a metal body having a proximal portion and a distal portion with first and second arms having opposed inward facing surfaces. Each inward facing surface can have at least one protrusion formed thereon. The jaw insert can also include first and second housings on the first and second arms, respectively. The first and second housings can include opposed inward facing surfaces that each define a clip track extending therealong for seating a clip therein. The at least one protrusion on each of the first and second arms can extend through the inward facing surface of the first and second housings, respectively, such that the at least one protrusion on each of the first and second arms is configured to contact a clip seated in the clip track.

In one embodiment, the first and second housings can be overmolded onto the first and second arms, and in another embodiment, the first and second housings can be configured to be coupled to the first and second arms through one of adhesive, welding, and mechanical engagement means.

The protrusion can be configured to prevent longitudinal sliding of the first and second housings. In certain embodiments, the protrusion can be positioned at a substantial mid-portion of the clip track such that the protrusion is configured to engage a bend zone on a clip seated in the clip track.

The jaws can be formed from various materials. For example, the metal body can be made of a first material and the first and second housings can be made of a second material. The first material can have a modulus of elasticity that is greater than a modulus of elasticity of the second material.

The housings can include various other features. For example, each of the first and second housings can have a plurality of fingers protruding into the clip track configured for retaining a clip therein. In one aspect, the metal body can be made of a first material, the first and second housings can be made of a second material, and the plurality of fingers can be made of a third material. The third material can have a modulus of elasticity that is less than a modulus of elasticity of the first material and a modulus of elasticity of the second material.

In other embodiments, the inward facing surface of the first and second housings can include upper and lower rails that define the clip track. At least one cut-out can be formed in at least one of the upper and lower rails for allowing a user to view a clip seated in the clip track.

In another embodiment, a method of manufacturing a jaw assembly of a surgical clip applier is provided and can include forming a metal frame defining first and second jaws configured to grasp tissue therebetween. Each jaw can have an engagement feature thereon. The method can also include molding first and second housings around the first and second jaws, respectively, to form opposed inward facing surfaces having a clip track formed therein and extending therealong for receiving and guiding a clip into the jaws. The engagement feature can prevent sliding movement of the first and second housings relative to the first and second jaws.

In one embodiment, the engagement feature can be a protrusion that extends through the housing and that is configured to contact a clip seated in the clip track. Each housing can include upper and lower rails defining the clip track. At least one of the upper and lower rails can have at least one finger protruding into the clip track. The method can also include injection molding a third material into cavities formed in the clip track to form a plurality of fingers extending into the clip track.

BRIEF DESCRIPTION OF THE DRAWINGS

The invention will be more fully understood from the following detailed description taken in conjunction with the accompanying drawings, in which.

DETAILED DESCRIPTION

Figure 1:
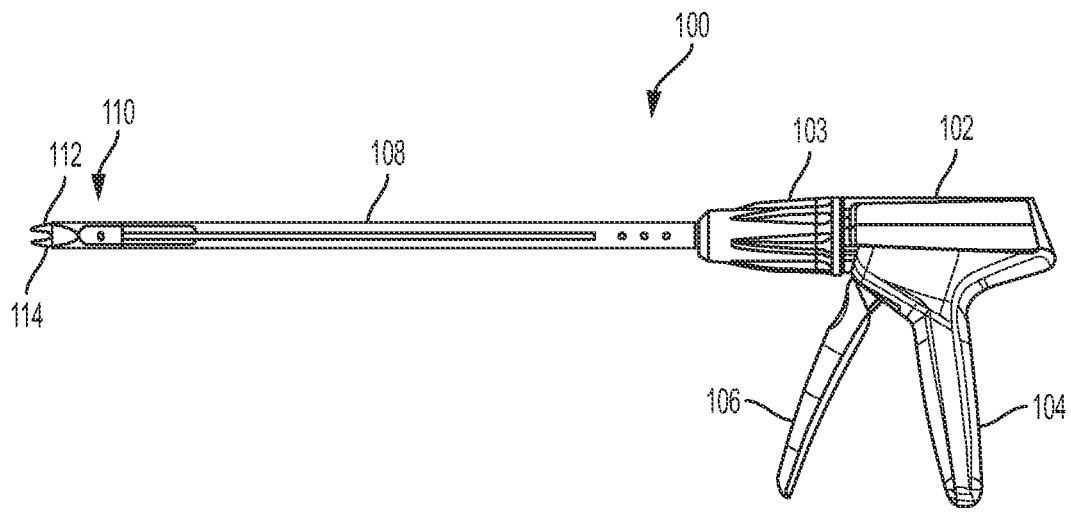
FIG. 1 is a side view of one exemplary embodiment of a surgical clip applier.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A surgical clip applier can generally be used to apply surgical clips to a vessel, duct, shunt, etc., during a surgical procedure. An exemplary surgical clip applier can include a jaw assembly having a frame with a pair of jaws and a housing overmolded onto the jaws with various clip aligning and engaging features. For example, the overmolded housing can have inward facing surfaces that define a clip track for receiving and guiding a clip into the jaws. The outer overmolded housing can allow for a variety of different structures and geometries to better control formation and placement of surgical clips that are not possible with other surgical clip appliers, such as clip appliers having jaws formed through a stamping or machining process.

A surgical clip applier can generally have a variety of different forms with a variety of different jaws and clip tracks. FIGS. 1-4B illustrate one embodiment of a surgical clip applier 100. A person skilled in the art will appreciate that the jaw assemblies disclosed herein can be used with any clip applier device, or with any device having jaws. The illustrated clip applier is merely one example of a device for use with the jaw assemblies disclosed herein, and it is not intended to be limiting. As shown, the surgical clip applier 100 generally includes a housing 102 having a stationary handle 104 and a movable handle or trigger 106 that is pivotally coupled to the housing 102. An elongate shaft 108 extends distally from the housing 102 and includes a jaw assembly 110 formed on a distal end 108d thereof and including first and second jaws 112, 114 that are movable between open and closed positions. The first and second jaws 112, 114 include opposed inward facing surfaces and each inward facing surface has a clip track formed therealong for receiving and guiding legs of a clip into the first and second jaws 112, 114. The elongate shaft 108 can be rotated with respect to the housing 102 via a rotation knob 103.

Figure 2:
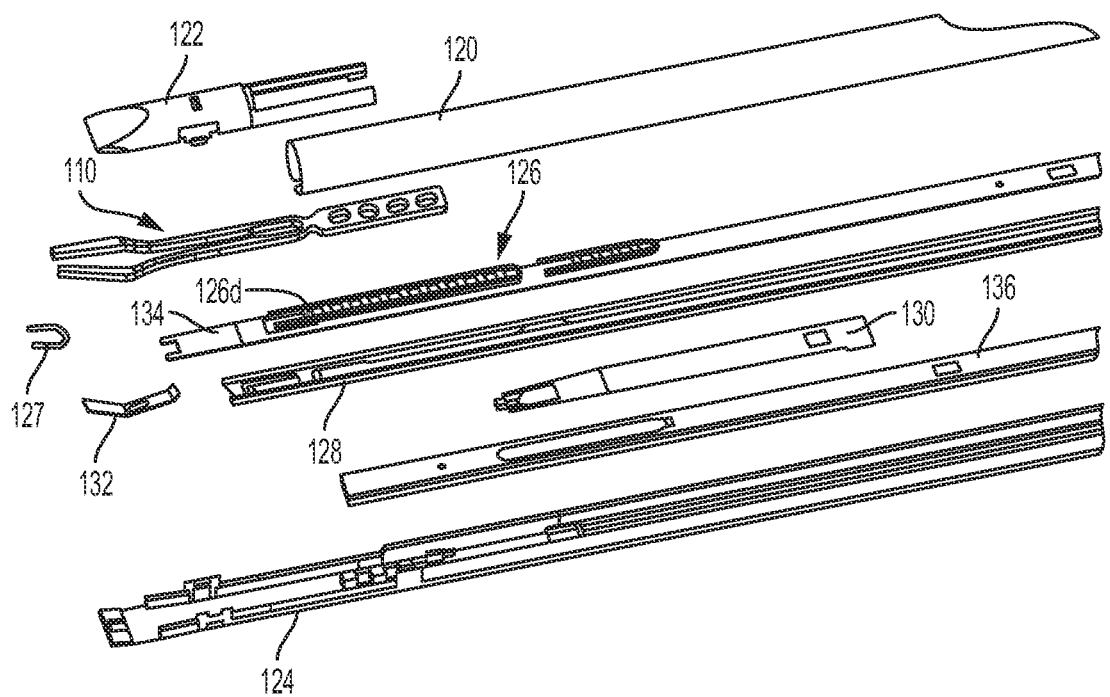
FIG. 2 is an exploded view of a distal portion of the surgical clip applier of FIG. 1.
Figure 3:
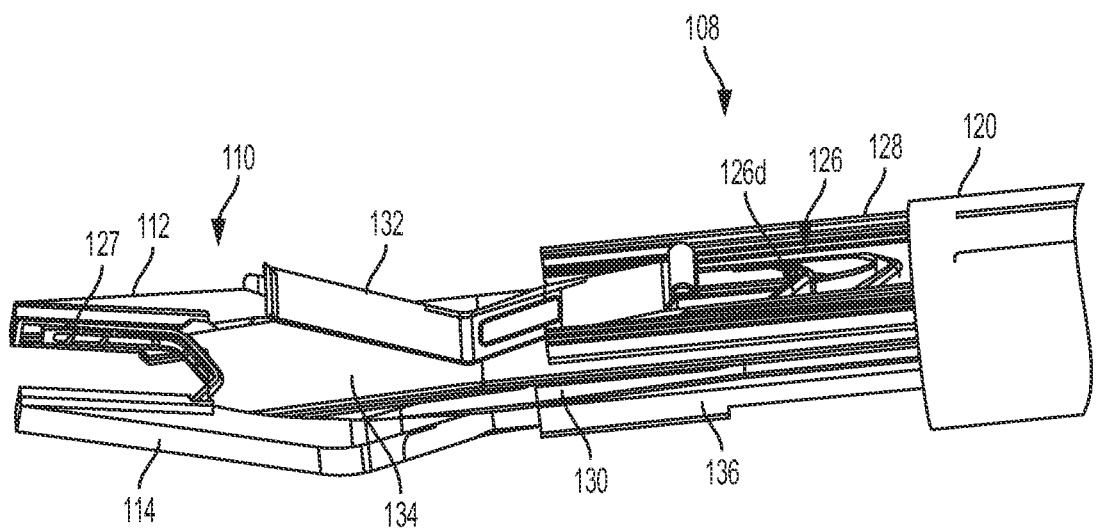
FIG. 3 is a perspective view of a distal portion of the surgical clip applier of FIG. 1.

As shown in FIGS. 2 and 3, the elongate shaft 108 can include an outer support tube 120, an upper shroud 122 coupled distally to the outer tube 120, and a lower shroud 124. The outer support tube 120 and the upper and lower shrouds 122, 124 form an outer casing of the shaft 108. As shown in FIGS. 2 and 3, a clip stack 126 including multiple surgical clips is disposed within a clip track or holder 128 of the shaft 108 proximal to the first and second jaws 112, 114, and is biased distally. A floor 130 extends beneath the clip stack 126 for maintaining the clip stack 126 in alignment within the shaft 108, and for guiding a distal-most clip 126d into the jaws 112, 114. A lifter spring 132 is positioned just proximal to the jaws 112, 114 and distal to the clip stack 126 for preventing distal movement of the clip stack 126, with the distal-most clip 126d disposed around the lifter spring 132. A feeder bar 134 extends through the elongate shaft 108 for feeding the distal-most clip 126d into the jaws. As shown in FIG. 3 illustrating the clip applier 100 with the upper and lower shrouds 122, 124 removed, a former tube 136 extends around a proximal end of the jaws 112, 114 and is movable distally to cam the jaws 112, 114 to a closed position for forming a clip 127 disposed therebetween.

Figure 4A:
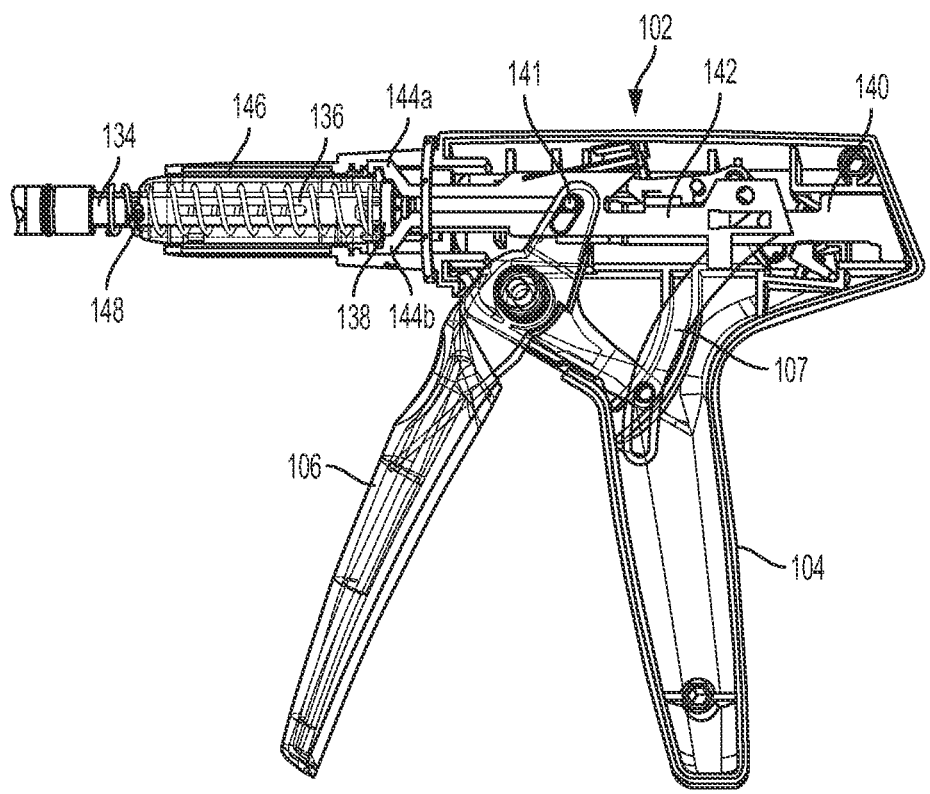
FIG. 4A is a perspective, partially transparent view of a proximal portion of the surgical clip applier of FIG. 1.
Figure 4B:
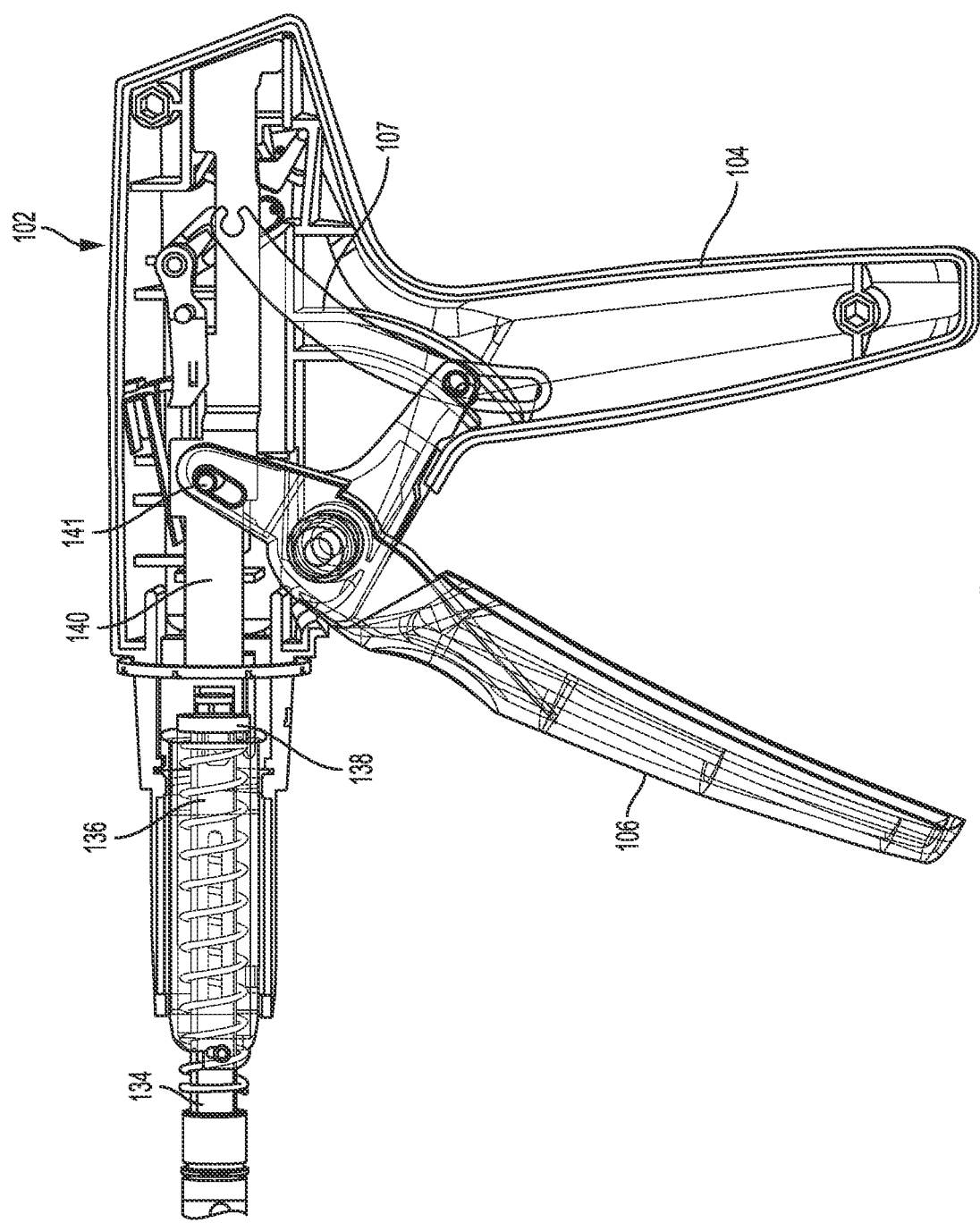
FIG. 4B is another perspective view of the proximal portion of the surgical clip applier of FIG. 1.

The surgical clip applier 100 has a clip forming assembly including various components that operate together to close the jaws 112, 114 when the trigger 106 is activated to thereby cause a clip (e.g., clip 127) disposed in the jaws to be applied (formed) to the tissue. The clip forming assembly encompasses the former tube 136 and other components that are coupled to the trigger 106 configured to be activated to move the former tube 136 distally to thereby close the jaws 112, 114. A clip advancing assembly of the surgical clip applier 100 includes the feeder bar 134 that is also coupled to the trigger 106, via a link 107 extending proximally from the trigger 106, as shown in FIGS. 4A and 4B. In this way, when the trigger 106 is activated, the feeder bar 134 is caused to move proximally, opposite to a distal direction in which the former tube 136 is moved upon activation of the trigger 106.

The clip forming and clip advancing assemblies can have any suitable configurations. For example, in the illustrated embodiment, as shown in FIGS. 4A and 4B, the former tube 136 of the clip forming assembly is coupled, via an inner coupling 138, to a former plate 140 in the handle 102 that is, in turn, coupled to the trigger 106 via a pin 141, and the feeder bar 134 of the clip advancing assembly is coupled to the trigger 106 via a feeder plate 142 that is also coupled to the trigger 106, via the link 107. As shown in FIG. 4A, the feeder plate 142 has arms 144*a*, 144*b* at a distal end thereof that are disposed over and mate with a proximal end of an outer coupling 146 (shown partially transparent). A connecting pin 148 at a distal end of the outer coupling 146 attaches the feeder bar 134 to the outer coupling 146. FIGS. 4A and 4B illustrate the handle 102 with part of an outer casing removed, and FIG. 4B shows the handle 102 without the feeder plate 142, for illustration purposes only. It should be appreciated that the surgical clip applier 100 can include various other components and assemblies that are not described herein for the sake of simplicity.

In use, when the trigger 106 of the handle 102 is activated (e.g., moved towards the stationary handle 104), the former plate 140 of the clip forming assembly is advanced distally to cause the former tube 136 to advance distally over the jaws 112, 114, thereby camming the jaws 112, 114 to the closed position. At the same time, the feeder plate 142 of the clip advancing assembly is moved proximally, thereby pulling the feeder bar 134 proximally to position the feeder bar 134 proximal of the distal-most clip 126*d* of the clip stack 126. Once the clip 127, disposed in the jaws 112, 114 such that clip's legs are received within the clip track of each of the jaws, is fully formed, the trigger 106 is released, which causes the clip forming assembly to move proximally while the clip advancing assembly moves distally. FIG. 2 shows the clip 127 in an original, pre-formed configuration. The proximal movement of the clip forming assembly causes the former tube 136 to retract relative to the jaws, thus allowing the jaws 112, 114 to move to the original open position, thereby releasing the formed clip. The distal movement of the clip advancing assembly causes the feeder bar 134 to move distally, and the feeder bar 134 thereby pushes the distal-most clip 126*d* distally, overcoming the biasing force of the lifter spring 132 and causing the lifter spring 132 to deflect out of the way, thereby allowing the distal-most clip 126*d* to be advanced into the jaws 112, 114. In this way, the distal-most clip becomes positioned in the jaws' clip track, like the clip 127 in FIG. 3. The floor 130 helps guide the distal-most clip into the clip tracks of the jaws 112, 114.

A person skilled in the art will appreciate that, while a trigger is shown and described, the clip appliers disclosed herein need not include a trigger, and can have a variety of other actuation mechanisms. For example, the clip applier can be powered and can include an actuation button for actuating a motor to control firing of the device. In other embodiments, the housing can be configured to couple to a robotic or telemanipulator system, such that actuation of the device is controlled through the robotic system.

A variety of different jaw assemblies incorporating various overmolded features can be used with a clip applier, such as the clip applier 100 illustrated in FIGS. 1-4A. The use of an overmolded housing can allow various features to be incorporated into the jaws that are not otherwise achievable using a typical stamping process for forming metal jaws.

Figure 5:
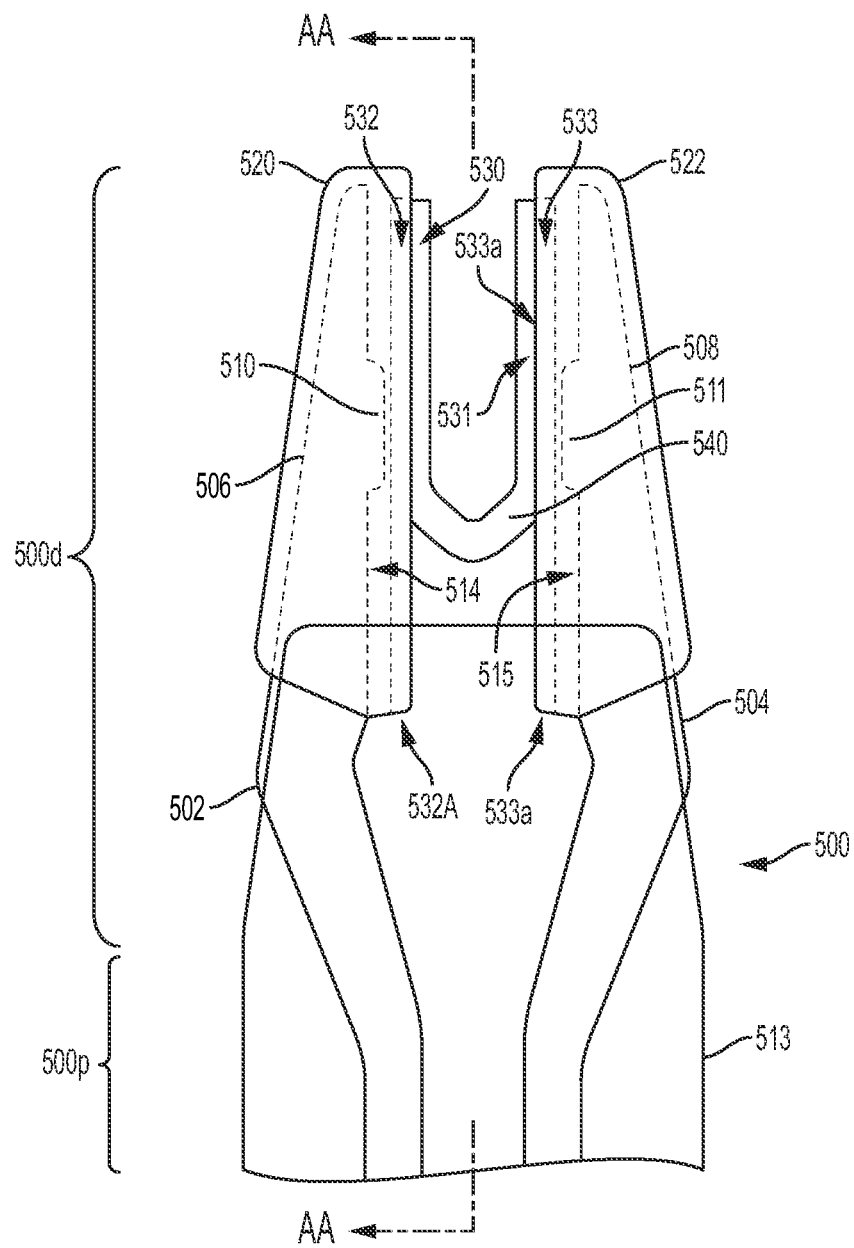
FIG. 5 is a side, transparent view of an embodiment of a portion of a jaw assembly for use with a surgical clip applier.
Figure 6:
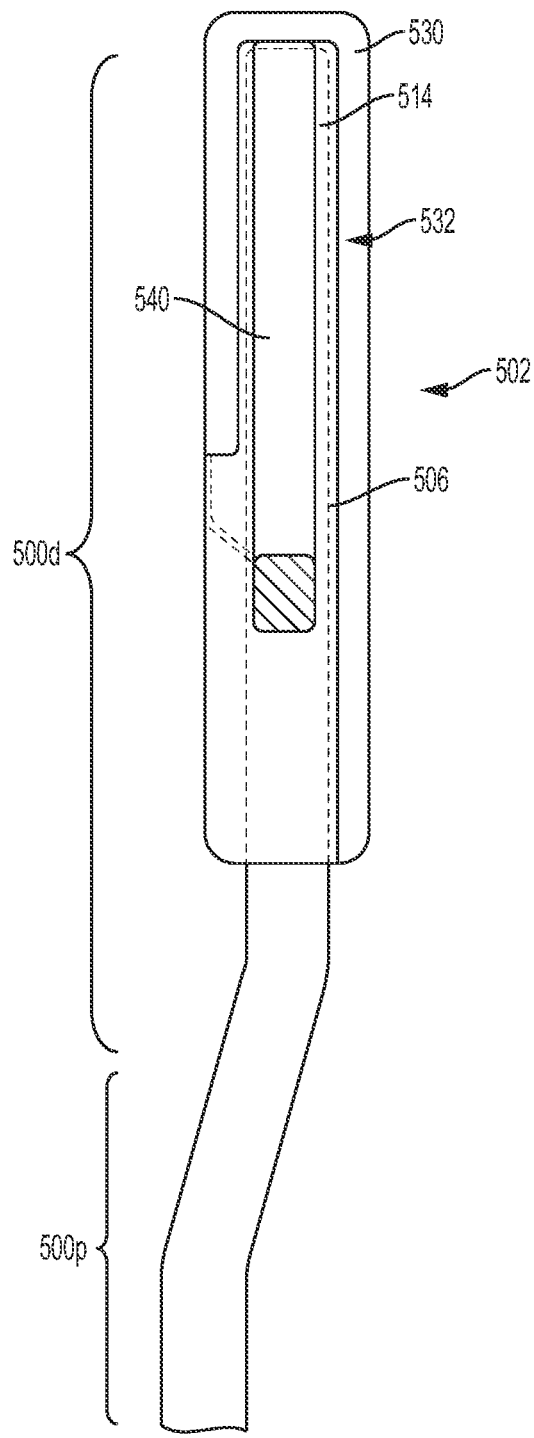
FIG. 6 is a front, transparent view of an inward facing surface of one of the jaws of the surgical clip applier in the direction AA of FIG. 5.

FIGS. 5 and 6 illustrate a portion of one embodiment of a jaw assembly 500 that can be used with a clip applier, such as the clip applier 100, and that can be configured to grasp tissue and form and apply surgical clips, similar to the first and second jaws 112, 114 discussed above regarding clip applier 100.

The illustrated jaw assembly 500 includes a frame having a proximal portion 500*p* (only a portion of which is shown) that is configured to extend into the distal end of an elongate shaft of a clip applier, and a distal portion 500*d* with first and second jaws 502, 504 forming an approximate Y-shape. The first and second jaws 502, 504 can each include a tip portion 506, 508 having opposed inward facing surfaces 514, 515 from which engagement features, such as protrusions 510, 511, can extend towards one another into a central opening of the Y-shape of the jaws 500. The protrusions 510, 511 can be configured to help retain the overmolded housing on each jaw 502, 504, as will be discussed in more detail below. In certain embodiments, the protrusions 510, 511 can also provide support to a clip seated within the jaws during clip formation, such as being configured to provide a rigid surface that can directly contact and compress a clip. In certain exemplary embodiments, the protrusions 510, 511 can be configured to contact a bend zone or curve in the clip configured to assist in clip formation and closure, as will also be discussed in more detail below. A shroud 513 similar to the upper shroud 122 can be provided.

The engagement features, such as protrusions 510, 511, can have a variety of shapes and sizes, and can be positioned at various locations. In the illustrate embodiment, the protrusions 510, 511 are generally rectangular in shape, and the protrusions 510, 511 extend across at least part of a height of the surface 514 or entirely across the height of the surface 541, and along a portion of the length of each tip portion 506, 508, in the proximal/distal direction. There can be one or more protrusions on each tip portion 506, 508.

The jaw frame can be formed from various materials, but in an exemplary embodiment the jaw frame is formed from a stamped, machined, Electrical Discharge Machining (EDM), or Direct Metal Laser Sintering (DMLS) metal. The metal can vary in hardness (or a material's resistance to indentation as measured by the modulus of elasticity scale), depending on desired properties of the material. The jaw frame should be sufficiently flexible to allow the jaws to move between opened and closed positions, while having sufficient stiffness to prevent deformation of the jaws when forces are applied thereto. Since the metal frame need not include clip tracks or other features for retaining a clip therein, the process for manufacturing the frame can be significantly simplified.

As indicated above, features can be formed around the tip portion 506, 508 of the first and second jaws 502, 504. For example, features can be overmolded onto the tip portion or can be molded separately and attached to the tip portion by a variety of means, such as adhesives, laser weld, snap features, interference fit, etc. As illustrated in FIG. 5, overmolded housings 520, 522 can be formed over the tip portions 506, 508. The overmolded housings 520, 522 can partially or fully surround the tip portions 506, 508, and can include opposed inward facing surfaces 530, 531 positioning in alignment with the inward facing surfaces 514, 515 of the tip portions 506, 508. Each inward facing surface 530, 531 can have features that define, for example, a clip track 532, 533 extending longitudinally therealong for receiving and guiding legs of a clip 540 into the first and second jaws 502, 504. In certain embodiments, the clip tracks 532, 533 can be in the form of a generally rectangular-groove extending from a proximal end to a distal end of each inward facing surface 530, 531. Each clip track 532, 533 can be defined by opposed upper and lower rails (only one rail 532a, 533a on each clip track 532, 533 is shown) extending longitudinally along upper and lower edges of the inward facing surface 530, 531 of each housing 520, 522. The opposed legs of the clip 540 can thus extend between the rails such that the legs of the clip 540 are axially aligned with one another.

As indicated above, the protrusions 510, 511 can help prevent sliding movement of the overmolded housings 520, 522. For example, each protrusion 510, 511 can extend at least partially into the housing 520, 522 to thereby retain the housing on the jaws. This can be achieved during manufacturing by overmolding the housings 520, 522, e.g., using injection molding or other molding techniques, directly onto the tip portions 506, 508 such that the protrusions 510, 511 extend into the body of the housings 520, 522, thereby preventing movement of the housings 520, 522. The housings 520, 522 can be made with a variety of materials, such as various plastics, liquid crystal polymer (LCP), elastomers, etc., and can vary in hardness (or a material's resistance to indentation as measured by the modulus of elasticity scale), depending on desired properties of the material. In some embodiments, the modulus of elasticity of the overmolded housings 520, 522 can be less than a modulus of elasticity of at least the tip portions 506, 508 of the first and second jaws 502, 504.

Figure 8:
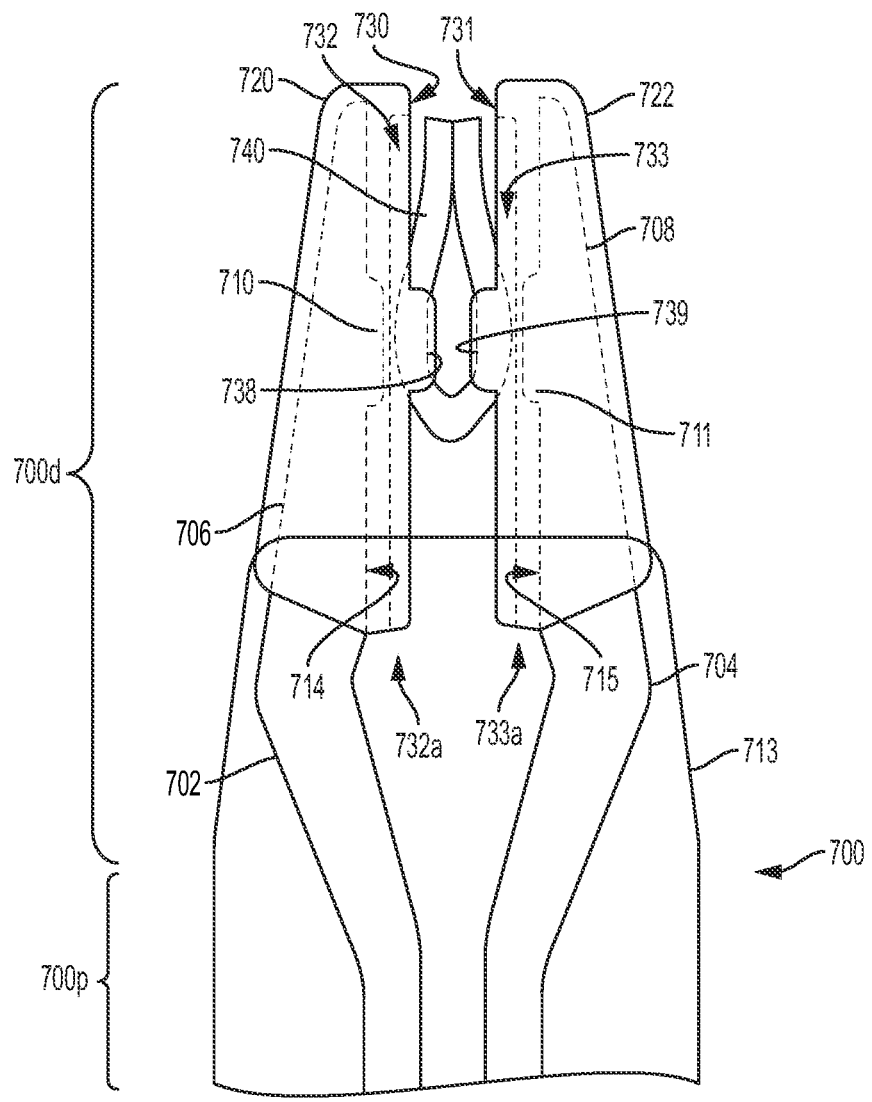
FIG. 8 is a side, transparent view of another embodiment of a portion of a jaw assembly for use with a surgical clip applier.

The protrusions 510, 511 can also assist in clip formation. In particular, the protrusions 510, 511 can be flush, can sit proud, or can be slightly subflush of the outer surface of each clip track 532, 533 such that the protrusions 510, 511 will contact a clip either directly or indirectly (while still providing structural support and a rigid surface) when the clip is seated in the clip tracks 532, 533. In an exemplary embodiment, the protrusions 510, 511 are flush with the outer surface so that the protrusions 510, 511 directly contact a clip seating in the clip track. As a result, the protrusions 510, 511 can provide a rigid surface for applying a force directly to the clips to aid in clip formation. In an exemplary embodiment, each protrusion 510, 511 is positioned to engage a bend zone of the clip, e.g., a region where the clip bends to move from the open configuration to the closed configuration. This is illustrated in FIG. 8, which shows protrusions 710, 711 located at about a mid-portion along the length of each tip portion and in contact with the bend zone. In other embodiments, the housings 520, 522 can be molded separately and attached to the tip portions 506, 508 by a variety of means, such as adhesives, laser welding, snap features, interference fit, etc.

In use, a clip advancing assembly can advance a clip 540 distally into the jaws 502, 504 such that the legs of the clip 540 are received within the clip track 532, 533 of each of the jaws 502, 504. The first and second jaws 502, 504 can move to the closed position, grasping tissue therebetween. This can be achieved using a former tube, for example, that is advanced around the jaws 502, 504, as previously discussed herein with respect to clip applier 100. When the jaws are closed, the clip 540 is compressed around tissue grasped therebetween. The protrusions 510, 511 act to provide additional structural force for deforming the clip 540 around the tissue.

Figure 7:
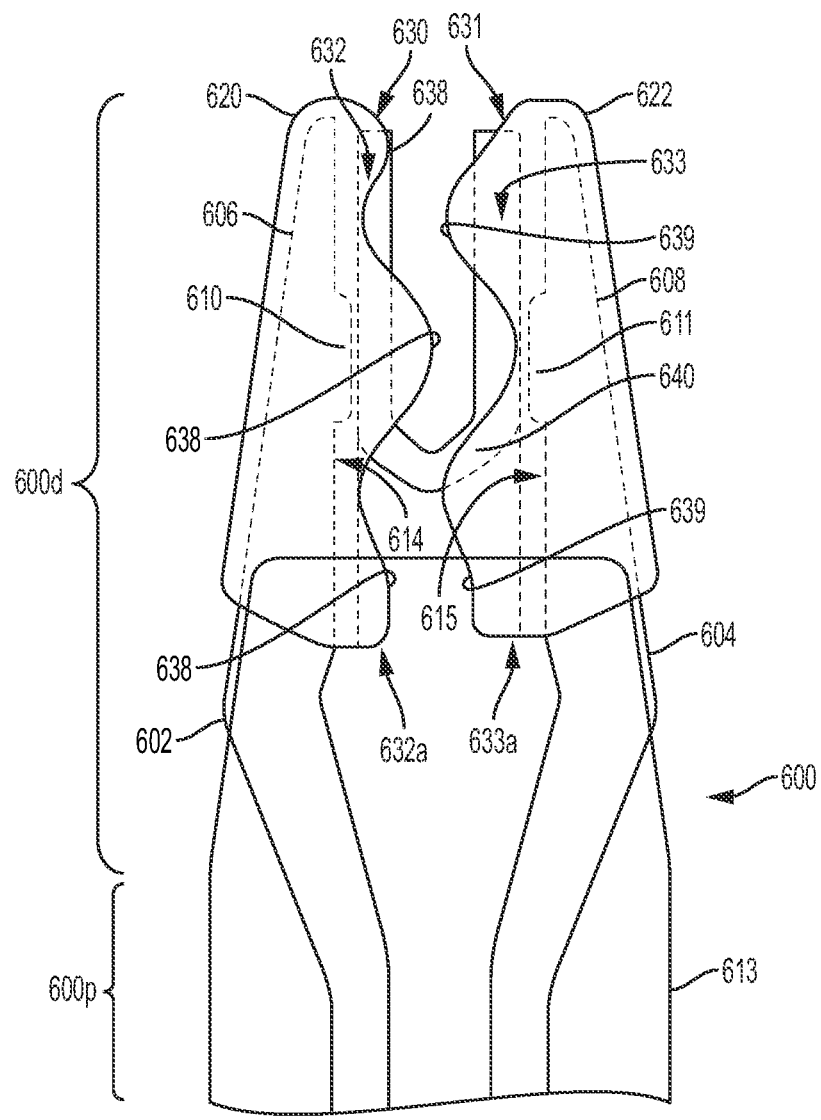
FIG. 7 is a side, transparent view of another embodiment of a portion of a jaw assembly for use with a surgical clip applier.

The overmolded housings can have a variety of features and structures formed thereon as injection molding materials onto the jaws can allow for a variety of geometries that are not possible when jaws are only stamped or machined. FIG. 7 illustrates another embodiment of a jaw assembly 600 with overmolded housings 620, 622, similar to jaw assembly 500 with overmolded housings 520, 522. The illustrated jaw assembly 600 has a frame with a proximal portion 600p (only a portion of which is shown) that is configured to extend into the distal end of an elongate shaft of a clip applier, and a distal portion 600d with first and second jaws 602, 604. The first and second jaws 602, 604 can each include a tip portion 606, 608 having opposed inward facing surfaces 614, 615 from which engagement features, such as protrusions 610, 611, can extend towards one another. Overmolded features can be formed over the tip portions 606, 608, such as the overmolded housings 620, 622 with opposed inward facing surfaces 630, 631. Each inward facing surface 630, 631 can have a clip track 632, 633 formed therealong for receiving and guiding legs of a clip 640. Each clip track 632, 633 can be defined by opposed upper and lower rails (only one rail 632a, 633a on each clip track 632, 633 is shown) extending longitudinally along upper and lower edges of the inward facing surface 630, 631 of each housing 620, 622. The opposed legs of the clip 640 can extend between the rails such that the legs of the clip 640 are axially aligned with one another. A shroud 613 similar to the upper shroud 122 can be provided.

In this embodiment, the opposed inward facing surfaces 630, 631 can also have ridges or protrusions 638, 639 formed on the upper and/or lower rails 632a, 633a that extend towards the opposed inward facing surface 630, 631 and surround the clip tracks 632, 633. As illustrated in FIG. 7, the protrusions 638, 639 can be configured to increase a depth of the clip tracks 632, 633 and/or to increase clip visibility while a clip is within the clip tracks 632, 633. The protrusions 638, 630 can also assist in grasping tissue to be clamped. The protrusions 638, 639 can be identical on each opposed jaw or can be complementary to one another for mating with one another when the jaws are closed. The protrusions 638, 639 can be made of the same material as the overmolded housings 620, 622 or can be made of a different material with a different modulus of elasticity, for example the protrusions 638, 639 can have a modulus of elasticity less than a modulus of elasticity of the material of the overmolded housings 620, 622, and thus less than a modulus of elasticity of the metal frame. When the protrusions 638, 639 are made of a different material, the overmolded housings 620, 622 can have cavities formed therein for receiving material for the protrusions 638, 639 during manufacturing.

While FIG. 7 illustrates a plurality of ridges or protrusions 638, 639 formed on the upper and lower rails that define the clip track, the overmolded housings 720, 722 can have a number of different protrusions or other features formed thereon. FIG. 8 illustrates another embodiment of a jaw assembly 700 with overmolded housings 720, 722, similar to jaw assembly 500 with overmolded housings 520, 522. The illustrated jaw assembly 700 can have a frame with a proximal portion 700p (only a portion of which is shown)

that is configured to extend into the distal end of an elongate shaft of a clip applier, and a distal portion 700d with first and second jaws 702, 704. The first and second jaws 702, 704 can each include a tip portion 706, 708 having opposed inward facing surfaces 714, 715 from which engagement features, such as protrusions 710, 711, can extend towards one another. Overmolded features can be formed over the tip portions 706, 708, such as overmolded housings 720, 722 with opposed inward facing surfaces 730, 731. Each inward facing surface 730, 731 can have a clip track 732, 733 formed therealong for receiving and guiding legs of a clip 740. Each clip track 732, 733 can be defined by opposed upper and lower rails (only one rail 732a, 733a on each clip track 732, 733 is shown) extending longitudinally along upper and lower edges of the inward facing surface 730, 731 of each housing 720, 722. The opposed legs of the clip 740 can extend between the rails such that the legs of the clip are axially aligned with one another. A shroud 713 similar to the upper shroud 122 can be provided.

The opposed inward facing surfaces 730 can have protrusions 738, 739 formed thereon that extend towards the opposed inward facing surface 730, 731, similar to the protrusions 638, 639. However, in this embodiment the protrusions 738, 739 can extend from the upper and/or lower rails 632a, 633a around the protrusions 710, 711, and can be configured to increase retention of the clip 740 within the jaw assembly 700 and help prevent clip fallout during formation. In other words, upper and lower protrusions on the upper and lower rails of each clip track can define a gap therebetween that is less than a height of the clip track, such that the upper and lower protrusions will help engage a clip seated therebetween. The protrusions 738, 739 can be made of the same material as the overmolded housings 720, 722 or can be made of a different material with a different modulus of elasticity, for example having a modulus of elasticity less than the material of the overmolded housings 720, 722. When the protrusions 738, 739 are made of a different material, the overmolded housings 720, 722 can have cavities formed therein for receiving material for the protrusions 738, 739 during manufacturing.

Figure 9:
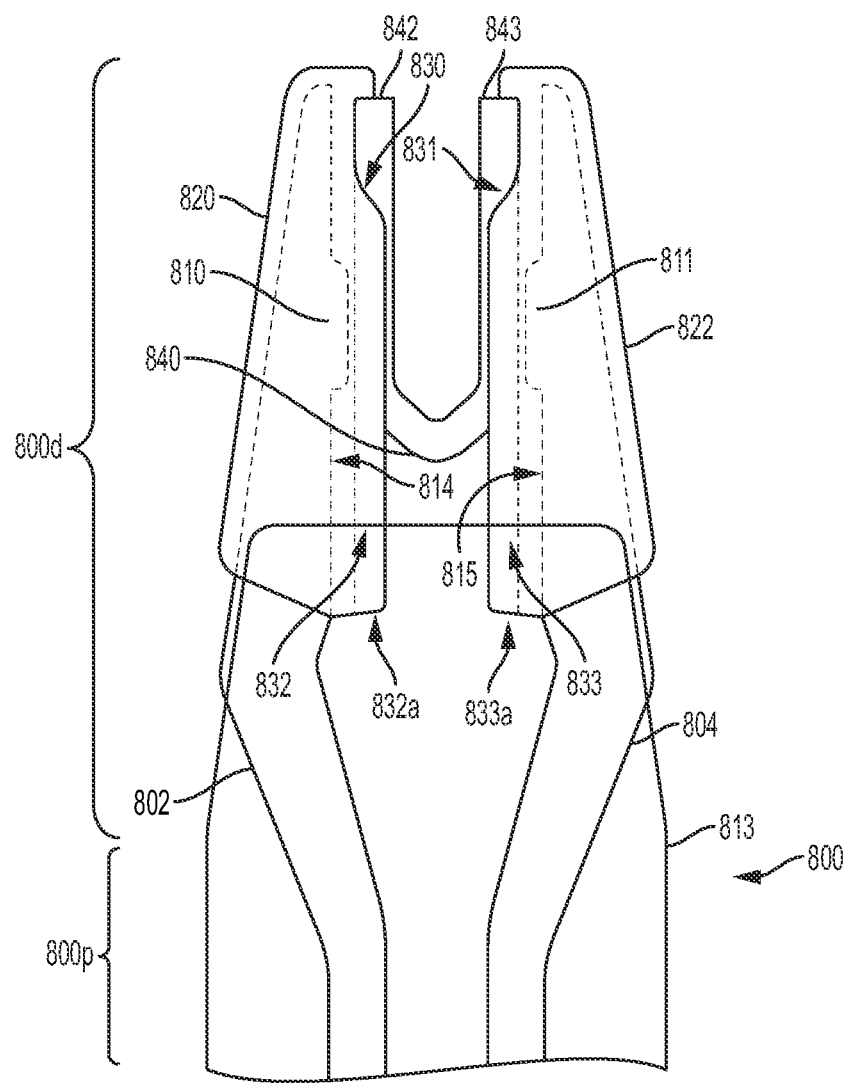
FIG. 9 is a side, transparent view of another embodiment of a portion of a jaw assembly for use with a surgical clip applier.

In other embodiments, various windows or openings can be formed in overmolded housings along clip tracks to allow users to view a location of a clip therein. As discussed above, the protrusions 638 can be configured to increase clip visibility while a clip is within the clip track 632, but openings can be formed anywhere along a length of the clip track. FIG. 9 illustrates a jaw assembly 800 with overmolded housings 820, 822, similar to jaw assembly 500 with overmolded housings 520, 522. The illustrated jaw assembly 800 has a frame with a proximal portion 800p (only a portion of which is shown) that is configured to extend into the distal end of an elongate shaft of a clip applier, and a distal portion 800d with first and second jaws 802, 804. The first and second jaws 802, 804 can each include a tip portion 806, 808 having opposed inward facing surfaces 814, 815 from which engagement features, such as protrusions 810, 811, can extend towards one another. Overmolded features can be formed over the tip portions 806, 808, such as the overmolded housings 820, 822 with opposed inward facing surfaces 830, 831. Each inward facing surface 830, 831 can have a clip track 832, 833 formed therealong for receiving and guiding legs of a clip 840. Each clip track 832, 833 can be defined by opposed upper and lower rails (only one rail 832a, 833a on each clip track 832, 833 is shown) extending longitudinally along upper and lower edges of the inward facing surface 830, 831 of each housing 820, 822. The opposed legs of the clip 840 can extend between the rails such that the legs of the clip are axially aligned with one another. A shroud 813 similar to the upper shroud 122 can be provided.

In this embodiment, the overmolded housings 820, 822 can have openings formed therein, for example openings formed in proximal and/or distal portions of the upper and/or lower rails. FIG. 9 illustrates openings formed in distal ends of the upper and lower rails 832a, 833a, however the openings can be formed at any location that allows for visibility of a clip seating in the clip tracks. In the illustrated embodiment, ends 842, 843 of the clip 840 can be seen by a user through the distal window to thereby increase visibility of the clip 840 and assist with alignment during placement.

Figure 10:
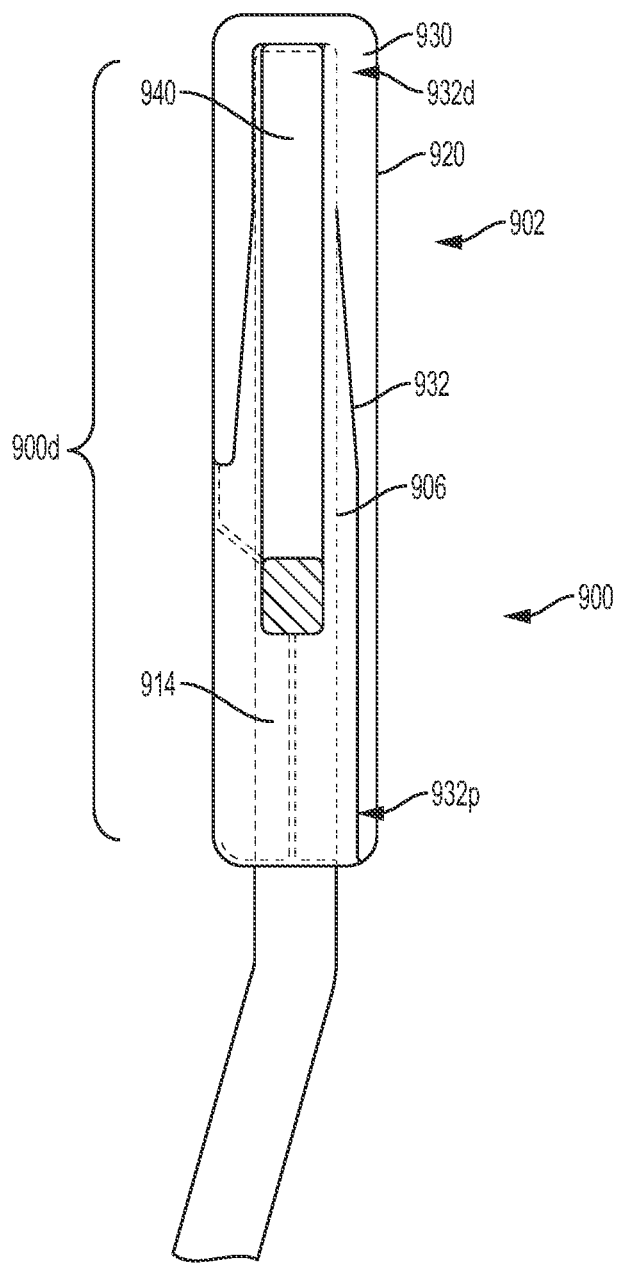
FIG. 10 is a front, transparent view of an inward facing surface of another embodiment of a jaw.

The clip track can also have a variety of configurations because of the injection molding process that are not possible with jaws that are stamped or machined. FIG. 10 illustrates another embodiment of a jaw assembly 900 with overmolded housings (with only one jaw and overmolded housing 920 being illustrated), similar to jaw assembly 500 with overmolded housings 520, 522. While only shown in part, the illustrated jaw assembly 900 has a frame with a proximal portion that is configured to extend into the distal end of an elongate shaft of a clip applier, and a distal portion 900d with first and second jaws (with only the first jaw 902 being illustrated, and the second jaw being a mirror image of the first jaw 902). The first and second jaws 902 can each include a tip portion 906 having opposed inward facing surfaces 914 from which engagement features, such as protrusions (not illustrated), can extend towards one another. Overmolded features can be formed over the tip portions 906, such as the overmolded housings 920 with opposed inward facing surfaces 930. Each inward facing surface 930 can have a clip track 932 formed therealong for receiving and guiding legs of a clip 940. Each clip track 932 can be defined by opposed upper and lower rails extending longitudinally along upper and lower edges of the inward facing surface 930 of each of the first and second housings 920. The opposed legs of the clip 940 can extend between the rails such that the legs of the clip are axially aligned with one another.

In this embodiment, the clip track 932 is tapered distally with a wider portion of the clip track 932 on a proximal end 932p thereof closer to a clip applier and a narrower portion of the clip track 932 on a distal end 932d thereof. The taper in the clip track 932 can be configured to allow easy and effective feeding of the clip 940 into the clip track 932 while also reducing clearance between the clip 940 and the clip track 932 as the clip 940 is fully fed into the clip track 932 and approaches the distal end 932d thereof. Widths of distal and proximal ends of the tapered clip track 932 can vary, for example a width of the clip track 932 at the proximal end 932p can be approximately double a width of the clip track 932 at the distal end 932d.

Figure 11:
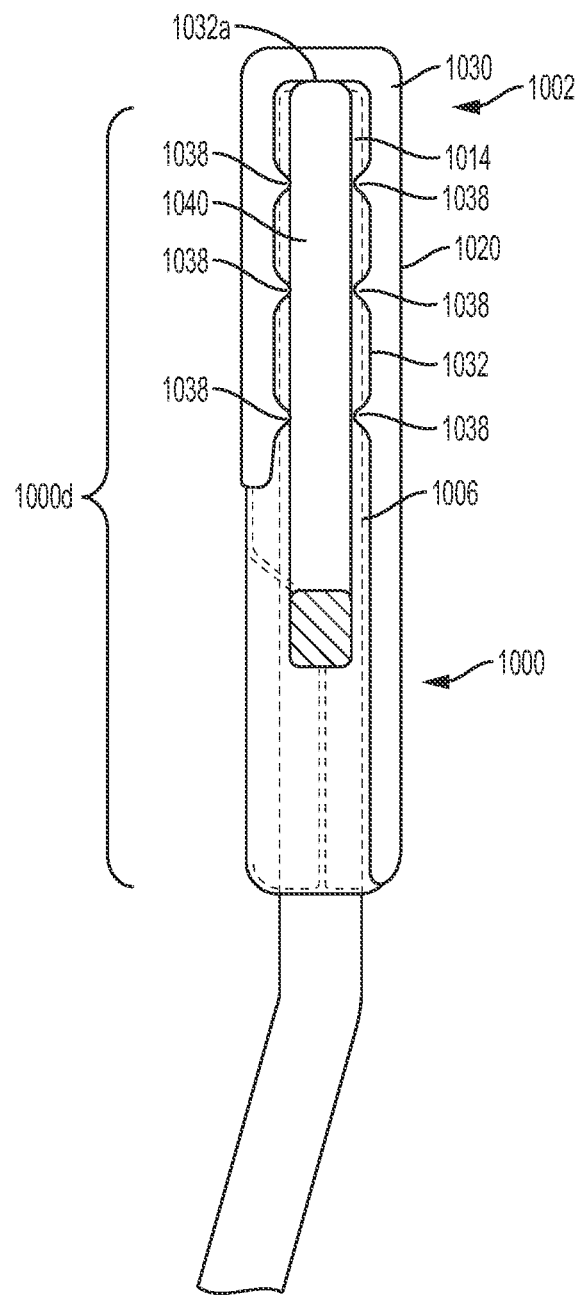
FIG. 11 is a front, transparent view of an inward facing surface of yet another embodiment of a jaw.

Protrusions can also extend into the clip track itself. FIG. 11 illustrates another embodiment of a jaw assembly 1000 with overmolded housings (with only one jaw and overmolded housing 1020 being illustrated), similar to jaw assembly 500 with overmolded housings 520, 522. The illustrated jaw assembly 1000 can have a frame with a proximal portion that is configured to extend into the distal end of an elongate shaft of a clip applier, and a distal portion 1000d with first and second jaws (with only the first jaw 1002 being illustrated, and the second jaw being a mirror image of the first jaw 1002). The first and second jaws 1002 can each include a tip portion 1006 having opposed inward facing surfaces 1014 from which engagement features, such as protrusions (not illustrated), can extend towards one another. Overmolded features can be formed over the tip portions 1006, such as the overmolded housings 1020 with opposed inward facing surfaces 1030. Each inward facing surface 1030 can have a clip track 1032 formed therealong for receiving and guiding legs of a clip 1040. Each clip track 1032 can be defined by opposed upper and lower rails extending longitudinally along upper and lower edges of the inward facing surface 1030 of each of the first and second housings 1020. The opposed legs of the clip 1040 can extend between the rails such that the legs of the clip are axially aligned with one another.

As shown, protrusions 1038 can be formed at various locations along the clip track 1032, for example being formed on and extending from each of the rails, and configured to extend into the clip track 1032 and engage the clip 1040 therein. The protrusions 1038 can be configured to assist in holding and aligning the clip 1040 in the clip track 1032 during formation. The protrusions 1038 can take a variety of forms, such as flexible fingers, pegs, fins, pads, wedges, etc., and there can be one or more protrusions 1038 formed in the clip track 1032. Widths, lengths, and stiffness levels (modulus of elasticity) of the protrusions 1038 can vary depending on desired uses. For example, the protrusions 1038 can have lengths such that a clip entering the clip track 1032 will be engaged by protrusions 1038 on either side of the clip track 1032 and be forced into an aligned, middle position in the clip track 1032, and the protrusions 1038 can be configured to flex or bend out of the way of a clip as it advances along the clip track 1038. This can be beneficial with surgical clips that have widths that vary along a length of the clip itself. The protrusions 1038 can be made of the same material as the overmolded housing 1020 or can be made of a different material with a different modulus of elasticity, for example having a modulus of elasticity less than a modulus of elasticity of the material of the overmolded housing 1020 to allow the protrusions 1038 to bend and flex with the clip 1040 while the housing 1020 provides stiffer support. When the protrusions 1038 are made of a different material, the overmolded housing 1020 can have cavities formed therein for receiving material for the protrusions 1038 during manufacturing.

Figure 12:
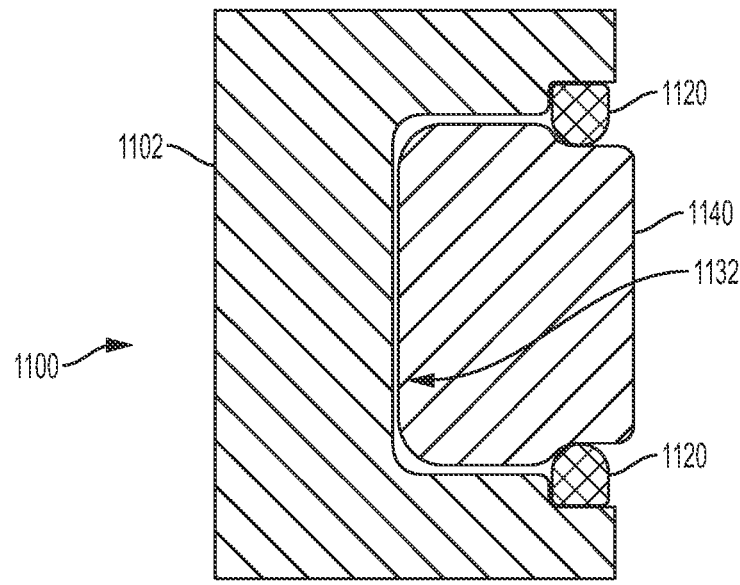
FIG. 12 is a cross-sectional view of another embodiment of a jaw.

Additional features can be added to a clip applier to improve clip retention in a jaw using an overmolded process, for example to keep a clip securely in a clip track with high clip retention forces while still having strong clip forming abilities. FIG. 12 illustrates another embodiment of a jaw assembly 1100 with overmolded housings (with only a cross-section of one jaw 1102 and overmolded features 1120 being illustrated), similar to jaw assembly 500 with overmolded housings 520, 522. The jaw 1102 of the illustrated jaw assembly 1100 is rigid and has overmolded features 1120 in the form of polymer rails formed thereon. As a clip 1140 is inserted into the jaw 1102, the polymer rails of the overmolded features 1120 can be configured to deform only slightly and allow for the clip 1140 to snap into place, being configured to keep the clip 1140 retained more securely against the jaw 1102 than many common designs that use only metal jaws. As illustrated in FIG. 12, the clip 1140 is configured to sit securely in a clip track 1132 of the jaw 1102.

Figure 13:
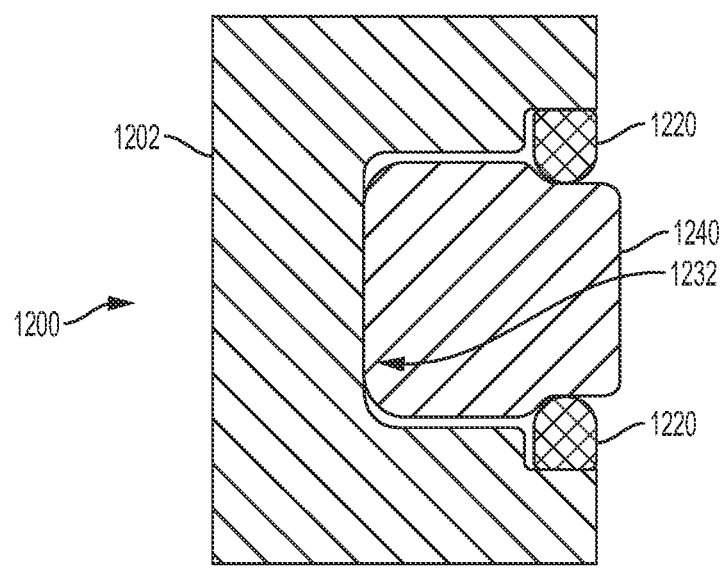
FIG. 13 is a cross-sectional view of still another embodiment of a jaw.

Another embodiment with a similar structure is illustrated in FIG. 13. A jaw assembly 1200 with overmolded housings (with only a cross-section of one jaw 1202 and overmolded features 1220 being illustrated), similar to jaw assembly 500 with overmolded housings 520, 522. The jaw 1202 of the illustrated jaw assembly 1200 is rigid and has overmolded features 1220 in the form of elastomer rails formed thereon. As a clip 1240 is inserted into the jaw 1202, the elastomer rails of the overmolded features 1220 can be configured to deform and allow for the clip 1240 to deform the overmolded features 1220 and secure itself into place. As illustrated in FIG. 13, the clip 1240 is configured to sit securely in a clip track 1232 of the jaw 1202. The elastomer rails of the overmolded features 1220 can have a lower modulus of elasticity than a modulus of elasticity of the polymer rails of the overmolded features 1120. The overmolded features 1120 can thus cause the clip 1140 to snap into place in the jaw 1102 while the overmolded features 1220 allow for more deformation of the elastomer rails and an easier release of the clip 1240.

Figure 14:
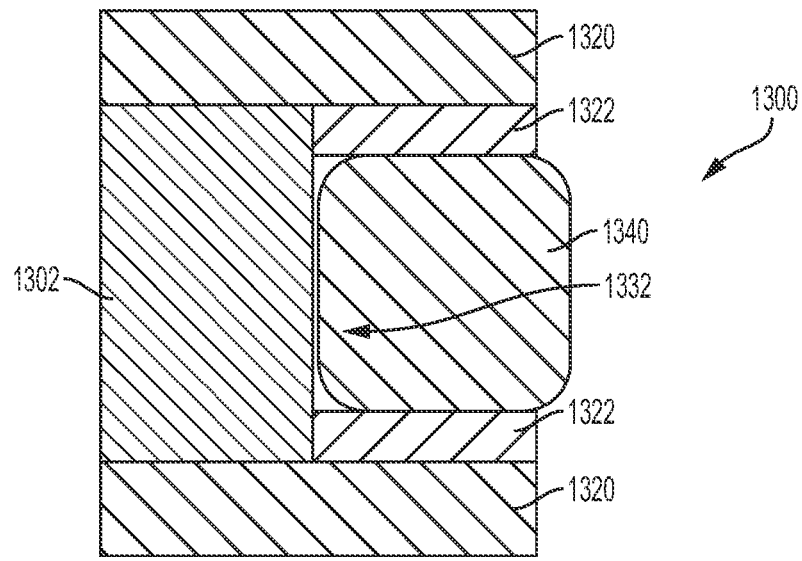
FIG. 14 is a cross-sectional view of another embodiment of a jaw.

FIG. 14 illustrates another embodiment of a jaw assembly 1300 with overmolded housings (with only a cross-section of one jaw 1302 and overmolded features 1320, 1322 being illustrated), similar to jaw assembly 500 with overmolded housings 520, 522. The jaw 1302 of the illustrated jaw assembly 1300 is rigid and has first overmolded features 1320 in the form of polymer sidewall rails formed on either side of the jaw 1302 and second overmolded features 1322 in the form of elastomer inserts formed in a clip track 1332. As a clip 1340 is inserted into the jaw 1302, the polymer sidewall rails of the overmolded features 1320 can be configured to guide the clip 1340 along the clip track 1332, providing a rigid guide. The elastomer inserts can be positioned in the clip track 1332 itself and provide an interference fit between the clip 1340 and the clip track 1332 so that the clip 1340 can sit securely in the clip track 1323 while benefiting from a rigid guide from the overmolded features 1320 because the polymer sidewalls of the overmolded features 1320 can have a higher modulus of elasticity than a modulus of elasticity of the elastomer inserts of the overmolded features 1322.

Figure 15:
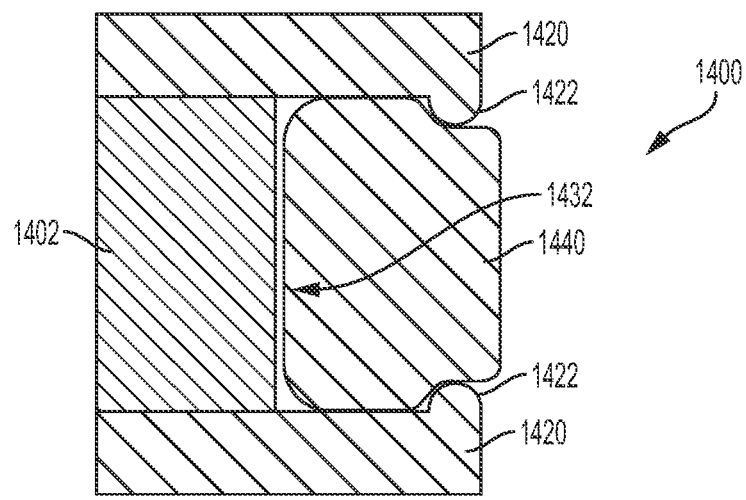
FIG. 15 is a cross-sectional view of yet another embodiment of a jaw.

While various structures are provided above for overmolded features, additional features and structures are possible. For example, FIG. 15 illustrates another embodiment of a jaw assembly 1400 with overmolded housings (with only a cross-section of one jaw 1402 and overmolded features 1420 being illustrated), similar to jaw assembly 500 with overmolded housings 520, 522. The jaw 1402 of the illustrated jaw assembly 1400 is rigid and has overmolded features 1420 in the form of polymer sidewall rails formed on either side of the jaw 1402 with arms 1422 formed to extend slightly into a clip track 1432 and help secure a clip 1440 therein.

Figure 16:
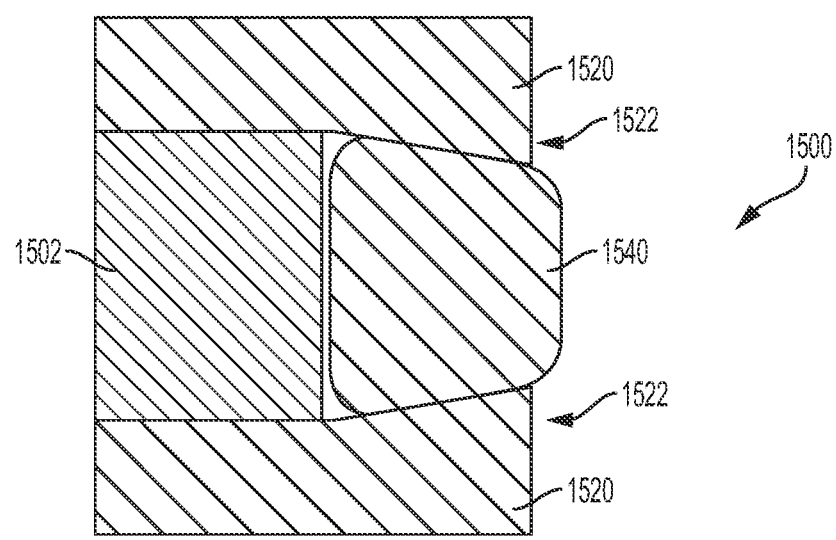
FIG. 16 is a cross-sectional view of still another embodiment of a jaw.

Another possible geometry is illustrated in FIG. 16, in which another embodiment of a jaw assembly 1500 with overmolded housings (with only a cross-section of one jaw 1502 and overmolded features 1520 being illustrated), similar to jaw assembly 500 with overmolded housings 520, 522. The jaw 1502 of the illustrated jaw assembly 1500 is rigid and has overmolded features 1520 in the form of polymer sidewall rails formed on either side of the jaw 1502 in a dovetail shape such that inner surfaces 1522 of the sidewall rails are thicker than outer surfaces and are thus configured to extend slightly into a clip track 1532 to help secure a clip 1540 therein. While the materials discussed herein are polymers and elastomers, any materials can be used that can have lower values for modulus of elasticity than the rigid jaws.

The various clip retaining features disclosed herein can have a variety of other configurations, as disclosed in U.S. application Ser. No. 15/674,075, filed on even date herewith and entitled "Clip Retention for Surgical Clip Applier," which is hereby incorporated by reference in its entirety.

During manufacturing, a rigid frame defining one of the jaws 500, 600, 700, 800, 900, 1000 discussed above can be stamped from a rigid material, such as metal, including the one or more protrusions extending from distal portions thereof. Housings defining the overmolded housings 520, 522, 620, 622, 720, 722, 820, 822, 920, 1020 can be formed by injection molding a material, such as various plastics, liquid crystal polymer (LCP), elastomer, etc., around each of the corresponding jaws 500, 600, 700, 800, 900, 1000 to form the housings with the opposed inward facing surfaces defining the clip tracks therein. The protrusions on the metal frame can prevent sliding movement of the overmolded housings relative to the frame.

The various protrusions or other features of the overmolded housings 620, 622, 720, 722, 820, 822, 920, 1020 discussed above located around and/or within the clip tracks can either be formed of the same material as the overmolded housings 620, 622, 720, 722, 820, 822, 920, 1020 and can be injection molded simultaneously with the overmolded housings 620, 622, 720, 722, 820, 822, 920, 1020 or can be made from a different material, such as various plastics, liquid crystal polymer (LCP), elastomer, etc., and can be formed after injection molding of the overmolded housings 620, 622, 720, 722, 820, 822, 920, 1020 has been completed. In such an embodiment, material for the various protrusions of the overmolded housings 620, 622, 720, 722, 820, 822, 920, 1020 can be injection molded into cavities or spacings formed on the overmolded housings 620, 622, 720, 722, 820, 822, 920, 1020 and configured to receive material for the protrusions therein. In some embodiments, material used to injection mold the overmolded housings 620, 622, 720, 722, 820, 822, 920, 1020 can be varied within a single overmolded housing to create varying material properties within one overmolded housing, for example increasing friction in various molded parts of the molded housings 620, 622, 720, 722, 820, 822, 920, 1020. Injection molding can thus occur in one step or over multiple steps depending on a desired complexity of the overmolded housings and how many materials are to be used in the overmolded housings.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on the anatomy of the subject in which the devices will be used, the size and shape of components with which the devices will be used, and the methods and procedures in which the devices will be used. The figures provided herein are not necessarily to scale. Although the devices and methods disclosed herein are generally directed to surgical techniques, they can also be used in applications outside of the surgical field.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A surgical clip applier, comprising:
   an elongate shaft; and
   a jaw assembly coupled to a distal end of the elongate shaft, the jaw assembly including
   a metal frame having a proximal portion coupled to the elongate shaft and a distal portion including first and second jaws movable between open and closed positions for engaging tissue therebetween, the first and second jaws having opposed inward facing surfaces, and the first and second jaws each having an engagement feature formed thereon, and
   a first outer housing extending along and around the first jaw and a second outer housing extending along and around the second jaw, each of the first and second outer housings having a clip track formed therein and configured to contact and guide a clip into the jaws, each of the first and second housings having opposed non-planar and non-linear inward facing surfaces.

2. The surgical clip applier of claim 1, wherein the engagement feature is configured to prevent movement of the first and second outer housings relative to the metal frame.

3. The surgical clip applier of claim 1, wherein each inward facing surface of the first and second outer housings has the clip track formed therein and extending longitudinally therealong.

4. The surgical clip applier of claim 1, wherein the first and second outer housings are overmolded around the first and second jaws.

5. The surgical clip applier of claim 1, wherein the first and second outer housings are coupled to the first and second jaws through one of adhesive, welding, and mechanical engagement means.

6. The surgical clip applier of claim 1, wherein each engagement feature of the first and second jaws comprises a protrusion formed on the corresponding inward facing surface of the first or second jaw.

7. The surgical clip applier of claim 6, wherein the protrusion on each of the first and second jaws extends through the outer housing such that the protrusion is configured to contact a clip seated in the clip track.

8. The surgical clip applier of claim 1, wherein the first and second outer housings are formed from a polymeric material.

9. The surgical clip applier of claim 1, wherein the metal frame has a modulus of elasticity that is greater than a modulus of elasticity of a material forming the first and second outer housings.

10. The surgical clip applier of claim 1, wherein the first and second outer housings each include a plurality of fingers protruding into the clip track for retaining a clip therein.

11. The surgical clip applier of claim 1, wherein the first and second outer housings each include upper and lower rails that at least partially define the clip track.

12. The surgical clip applier of claim 11, wherein the first and second outer housings each have upper and lower protrusions positioned on opposed sides of the clip track for retaining a clip seated in the clip track.

13. A jaw insert for use with a clip applier device, comprising:
    a metal body having a proximal portion and a distal portion with first and second arms having opposed inward facing surfaces, each inward facing surface having at least one protrusion formed thereon; and
    first and second housings extending along and around the first and second arms, respectively, each of the first and second housings including a clip track extending therealong and configured to seat a clip therein, each of the first and second housings having opposed non-planar and non-linear inward facing surfaces.

14. The jaw insert of claim 13, wherein each of the opposed non-planar and non-linear inward facing surfaces include the corresponding clip track of the first or second housing extending therealong and configured to seat a clip therein, and the at least one protrusion on each of the first and second arms extends through the inward facing surface of the first and second housings, respectively, such that the at least one protrusion on each of the first and second arms is configured to contact a clip seated in the clip track.

15. The jaw insert of claim 13, wherein the first and second housings are overmolded onto the first and second arms.

16. The jaw insert of claim 13, wherein each of the protrusions is configured to prevent longitudinal sliding of the corresponding first or second housing.

17. The jaw insert of claim 13, wherein each of the protrusions is positioned at a substantial mid-portion of the corresponding clip track such that the protrusion is configured to engage a bend zone on a clip seated in the clip track.

18. The jaw insert of claim 13, wherein each of the inward facing surfaces of the first and second housings includes upper and lower rails that define the clip track.

19. The jaw insert of claim 13, wherein each of the first and second housings has a plurality of fingers protruding into the clip track configured for retaining a clip therein.

20. The jaw insert of claim 19, wherein the metal body is made of a first material, the first and second housings are made of a second material, and the plurality of fingers are made of a third material, the third material having a modulus of elasticity that is less than a modulus of elasticity of the first material and a modulus of elasticity of the second material.

* * * * *